United States Patent
Bhatnagar et al.

(10) Patent No.: US 6,291,459 B1
(45) Date of Patent: Sep. 18, 2001

(54) CALCILYTIC COMPOUNDS

(75) Inventors: Pradip Bhatnagar, Exton; Maria Amparo Lago, Audubon, both of PA (US)

(73) Assignee: SmithKline Beecham Corporation

( * ) Notice: Subject to any disclaimer, the term of this patent is extended or adjusted under 35 U.S.C. 154(b) by 0 days.

(21) Appl. No.: 09/762,413

(22) PCT Filed: Aug. 12, 1999

(86) PCT No.: PCT/US99/18378

§ 371 Date: Apr. 9, 2001

§ 102(e) Date: Apr. 9, 2001

(87) PCT Pub. No.: WO00/09132

PCT Pub. Date: Feb. 24, 2000

Related U.S. Application Data

(60) Provisional application No. 60/096,335, filed on Aug. 12, 1998.

(51) Int. Cl.[7] ............... A61K 31/5375; C07D 265/30

(52) U.S. Cl. ...................... 514/237.8; 544/162

(58) Field of Search .................. 544/162; 514/237.8

(56) References Cited

U.S. PATENT DOCUMENTS

| | | | |
|---|---|---|---|
| 4,226,865 | * 10/1980 | Burkard et al. | 424/248.5 |
| 4,252,801 | * 2/1981 | Hauck et al. | 424/246 |
| 4,923,863 | 5/1990 | Scopes et al. | 514/235.5 |
| 5,082,840 | * 1/1992 | Arch et al. | 514/233.5 |

* cited by examiner

*Primary Examiner*—Floyd D. Higel
*Assistant Examiner*—Golam M. M. Shameem
(74) *Attorney, Agent, or Firm*—Soma G. Simon; William T. King; Charles M. Kinzig

(57) ABSTRACT

A compound selected from Formula (I) hereinbelow:

Formula (I)

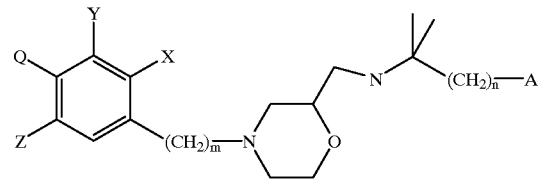

or a pharmaceutically acceptable salt thereof, wherein m is an integer from 0 to 2; n is an integer from 1 to 3;

X is selected from the group consisting of CN, $NO_2$, Cl, F, and H;

Y is selected from the group consisting of Cl, F, Br, I and H; and

Q and Z are, independently, selected from the group consisting of H, $R_1$, $SO_2R_1'$, $R_1C(O)OR_1''$, $SO_2NR_1'R_1''$, $C(O)NR_1'R_1''$, $NR_1'SO_2R''_1$, wherein R1, $R_1'$ and $R_1''$ are independently selected from the group consisting of hydrogen, $C_{1-4}$ alkyl, $C_{3-6}$ cycloalkyl, $C_{2-5}$ alkenyl, $C_{2-5}$ alkynyl, heterocycloalkyl, aryl and aryl $C_{1-4}$ alkyl; or $R_1'$ and $R_1''$ together form a 3 to 7 membered optionally substituted heterocyclic ring; wherein any substituents are selected from the group consisting of CN, aryl, $CO_2R$, $CO_2NHR$, OH, OR, $NH_2$, halo, $CF_3$, $OCF_3$ and $NO_2$; wherein R represents H, $C_{1-4}$ alkyl, and $C_{3-6}$ cycloalkyl; and A is phenyl or naphthyl, unsubstituted or substituted with any substituents being selected from the group consisting of OH, halo, $CO_2R_1$, $C_{1-4}$ alkyl, $C_{1-4}$ alkoxy, $C_{3-6}$ cycloalkyl, $OSO_2R_1$, CN, $NO_2$, $OCF_3$, $CF_3$, and $CH_2CF_3$, $(CH_2)_nCO_2H$, $(CH_2)_nCO_2R_1$, and $O-(CH_2)_n CO_2R_1$, wherein n is an integer from 0 to 3 0–3 and $R_1$ represents $C_{1-4}$ alkyl, $C_{3-6}$ cycloalkyl, $C_{3-6}$ cycloalkyl, heteroaryl or fused heteroaryl (wherein the hetero-ring can contain N, O or S and can be aromatic, dihydro or tetrahydro) unsubstituted or substituted with any substituents being selected from the group consisting of OH, $OCH_3$, $CH(CH_3)_2$, halo, $CO_2R_1$, $C_{1-4}$ alkyl, $C_{1-4}$ alkoxy, $C_{3-6}$cycloalkyl, CN, $NO_2$, $OCF_3$, $CF_3$, $CH_2CF_3$, $(CH_2)_n CO_2R_1$, and $O-(CH_2)_nCO_2R_1$ is provided.

7 Claims, No Drawings

CALCILYTIC COMPOUNDS

This application is a 371 of PCT/US99/18378 Aug. 12, 1999 and United States of America 60096335 Aug. 12, 1998.

FIELD OF INVENTION

The present invention relates to novel calcilytic compounds, pharmaceutical compositions containing these compounds and their use as calcium receptor antagonists.

In mammals, extracellular $Ca^{2+}$ is under rigid homeostatic control and regulates various processes such as blood clotting, nerve and muscle excitability, and proper bone formation. Extracellular $Ca^{2+}$ inhibits the secretion of parathyroid hormone ("PTH") from parathyroid cells, inhibits bone restoration by osteoclasts, and stimulates secretion of calcitonin from C-cells. Calcium receptor proteins enable certain specialized cells to respond to changes in extracellular $Ca^{2+}$ concentration.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ then acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in extracellular $Ca^{2+}$ has been confirmed. See Brown et al., Nature 366:574, 1993. In parathyroid cells, this protein the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, reviewed in Nemeth et al., Cell Calciuim 11:319, 1990. For example, extracellular $Ca^{2+}$ plays a role in parafollicular (C-cells) and parathyroid cells. See Nemeth, Cell Calcium 11:323, 1990. The role of extracellular $Ca^{2+}$ on bone osteoclasts has also been studied. See Zaidi, Bioscience Reports 10:493, 1990.

Various compounds are known to mimic the effects of extra-cellular $Ca^{2+}$ on a calcium receptor molecule. Calcilytics are compounds able to inhibit calcium receptor activity, thereby causing a decrease in one or more calcium receptor activities evoked by extracellular $Ca^{2+}$. Calcilytics are useful as lead molecules in the discovery, development, design, modification and/or construction of useful calcium modulators which are active at $Ca^{2+}$ receptors. Such calcilytics are useful in the treatment of various disease states characterized by abnormal levels of one or more components, e.g., polypeptides such as hormones, enzymes or growth factors, the expression and/or secretion of which is regulated or affected by activity at one or more $Ca^{2+}$ receptors. Target diseases or disorders for calcilytic compounds include diseases involving abnormal bone and mineral homeostasis.

Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

Thus, calcium receptor antagonists offer a unique approach towards the pharmacotherapy of diseases associated with abnormal bone or mineral homeostasis, such as hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

SUMMARY OF THE INVENTION

The present invention comprises novel calcium receptor antagonists represented by Formula (I) hereinbelow and their use as calcium receptor antagonists which are useful in the treatment of a variety of diseases associated with abnormal bone or mineral homeostasis, including but not limited to hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

The present invention further provides a method for antagonizing calcium receptors in an animal, including humans, which comprises administering to an animal in need thereof an effective amount of a compound of Formula (I), indicated hereinbelow.

The present invention further provides a method for increasing serum parathyroid levels in an animal, including humans, which comprises administering to an animal in need thereof an effective amount of a compound of Formula (I), indicated hereinbelow.

DETAILED DESCRIPTION OF THE INVENTION

The compounds of the present invention are selected from Formula (I) hereinbelow:

Formula (I)

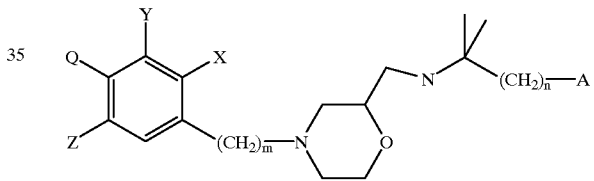

or a pharmaceutically acceptable salt thereof,
wherein:

m is an integer from 0 to 2;

n is an integer from 1 to 3;

X is selected from the group consisting of CN, $NO_2$, Cl, F, and H;

Y is selected from the group consisting of Cl, F, Br, I and H; and

Q and Z are, independently, selected from the group consisting of H,$R_1SO_2R_1$, $R_1C(O)OR_1"$, $SO_2NR_1'R_1"$, $C(O)NR_1'R_1"$, $NR_1'SO_2R"_1$, wherin R1, $R_1'$ and $R_1"$ are independently selected from the group consisting of hydrogen, $C_{1-4}$ alkyl, $C_{3-6}$ cycloalkyl, $C_{2-5}$ alkenyl, $C_{2-5}$ alkynyl, heterocycloalkyl, aryl and aryl $C_{1-4}$ alkyl; or $R_1'$ and $R_1"$ together form a 3 to 7 membered optionally substituted heterocyclic ring; wherein any substituents are selected from the group consisting of CN, aryl, $CO_2R$, $CO_2NHR$, OH, OR, $NH_2$, halo, $CF_3$, $OCF_3$ and $NO_2$; wherein R represents H, $C_{1-4}$ alkyl, and $C_{3-6}$ cycloalkyl: and A is phenyl or naphthyl, unsubstituted or substituted with any substituents being selected from the group consisting of OH, halo, $CO_2R_1$, $C_{1-4}$ alkyl, $C_{1-4}$ alkoxy, $C_{3-6}$ cycloalkyl, $OSO_2R_1$, CN, $NO_2$, $OCF_3$, $CF_3$, and $CH_2CF_3$, $(CH_2)_nCO_2H$, $(CH_2)_nCO_2R_1$, and $O-(CH_2)_nCO_2R_1$, wherein n is an integer from 0 to 3 0–3 and $R_1$ represents $C_{1-4}$ alky, $C_{3-6}$ cycloalkyl, $C_{3-6}$ cycloalkyl, heteroaryl or fused heteroaryl (wherein the hetero-ring can contain N, O or S and can be aromatic, dihydro or tetrahydro) unsubstituted or substituted with any substituents being selected from the group consisting of OH, $OCH_3$, $CH(CH_3)_2$, halo, $CO_2R_1$, $C_{1-4}$ alkyl, $C_{1-4}$ alkoxy, $C_{3-6}$cycloalkyl, CN, $NO_2$, $OCF_3$, $CF_3$, $CH_2CF_3$, $(CH_2)_nCO_2R_1$, and $O-(CH_2)_nCO_2R_1$.

As used herein, "alkyl" refers to an optionally substituted hydrocarbon group joined by single carbon-carbon bonds and having 1–20 carbon atoms joined together. The alkyl hydrocarbon group may be linear, branched or cyclic, saturated or unsaturated. The substituents are selected from F, Cl, Br, I, N, S and O. Preferably, no more than three substituents are present. More preferably, the alkyl has 1–12 carbon atoms and is unsubstituted. Preferably, the alkyl group is linear. Preferably, the alkyl group is saturated.

As used herein "lower alkyl" refers to $C_{1-5}$alkyl.

As used herein "cycloalkyl" refers to 3–7 membered carbocyclic rings.

As used herein "heterocycloalkyl" refers to 4, 5, 6 or 7 membered heterocyclic rings containing 1 to 2 heteroatoms selected from N, O and S.

The compounds of the present invention may contain one or more asymmetric carbon atoms and may exist in racemic and optically active forms. All of these compounds and diastereomers are contemplated to be within the scope of the present invention.

Preferred compounds of the present invention are selected from the group consisting of:

(R,S)-N-[4-(2-Nitro-4-trifluoromethylphenyl)morpholin-2-ylmethyl]-N-[1,1-dimethyl-2-(4-methoxyphenyl)] ethylamine; and (R,S)-N-[4-(2,3-Dichlorobenzyl)morpholin-2-ylmethyl]-N-[1,1-dimethyl-2-(4-methoxyphenyl)]ethylamine.

Pharmaceutically acceptable salts are non-toxic salts in the amounts and concentrations at which they are administered.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. A preferred salt is a hydrochloride. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present.

The present invention provides compounds of Formula (I) above which can be prepared using standard techniques. An overall strategy for preparing preferred compounds described herein can be carried out as described in this section. The examples which follow illustrate the synthesis of specific compounds. Using the protocols described herein as a model, one of ordinary skill in the art can readily produce other compounds of the present invention.

A general procedure used to synthesize many of the compounds is described in Schemes 1 and 2. Boc-2-carboxymorpholine can be coupled with the appropriate amine such as 1,1-dimethyl-2-(4-methoxyphenyl) ethylamine under standard conditions such as formation of the corresponding acid fluoride with cyanuric fluoride. Removal of the Boc protecting group can be carried out under standard conditions (TFA/dichloromethane, or HCl/dioxane)(Scheme 1). The unprotected morpholine derivative can be reacted with an appropriately substituted arylfluoride such as 4-fluoro-3-nitro-1-trifluoromethylbenzene, to obtain the corresponding arylamine. Alternatively (scheme 2), the amine can be alkylated by reacting with the appropriate alkyl halide or by reaction with the corresponding aldehyde under standard reductive amination conditions. Reduction or the amide bond to the amine with $BH_3.SMe_2$ can then lead to the final products.

Scheme I

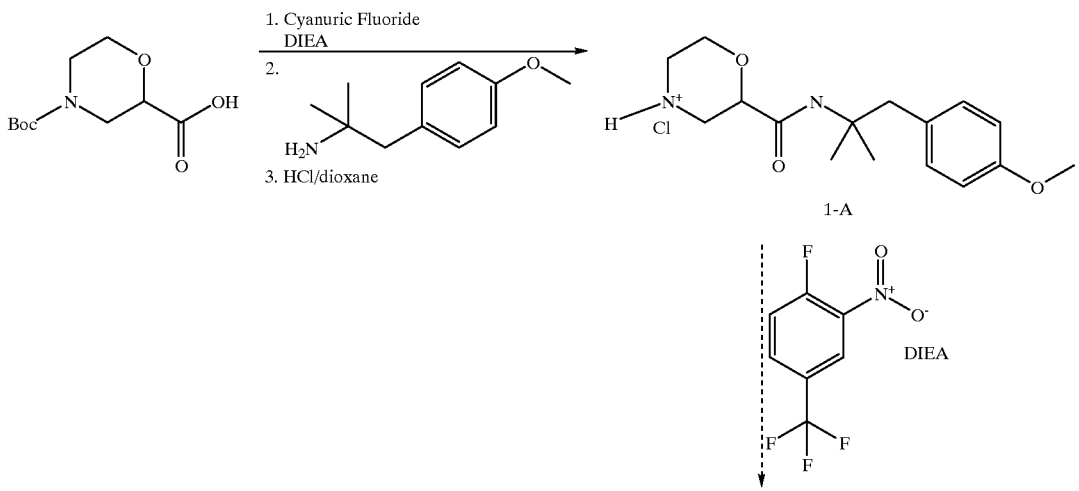

-continued

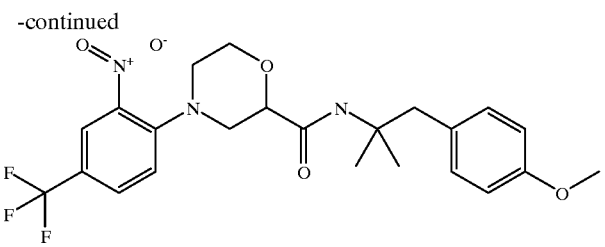

Scheme 2

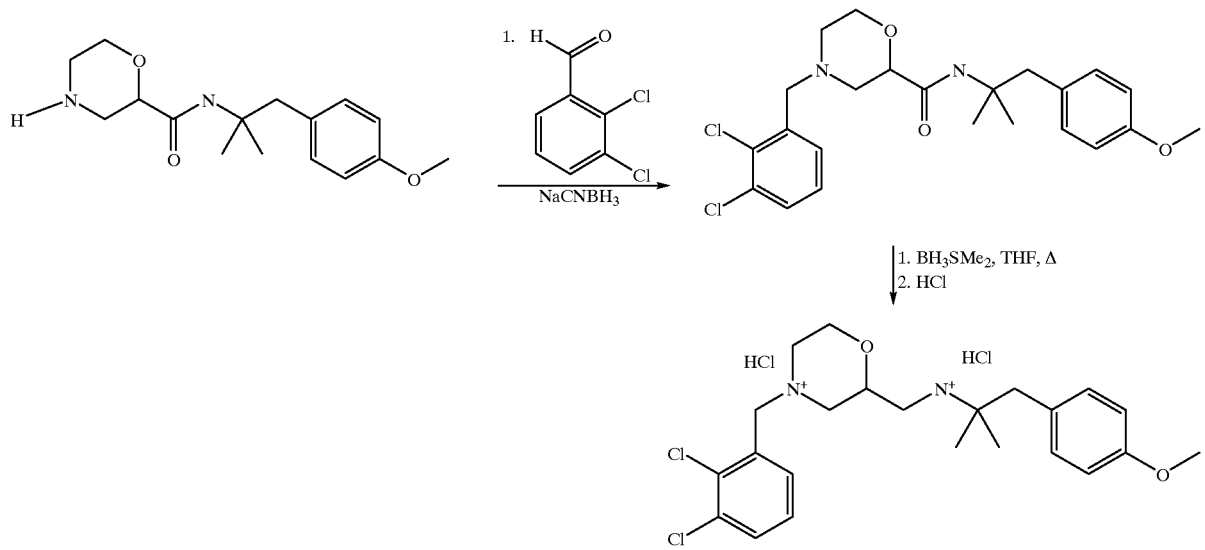

Nuclear magnetic resonance spectra were recorded at either 250 or 400 MHz using, respectively, a Bruker AM 250 or Bruker AC 400 spectrometer. CDCl$_3$ is deuteriochioroform, DMSO-d$_6$ is hexadeuteriodimethylsulfoxide, and CD$_3$OD is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers (cm$^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs ODS refers to an octadecylsilyl derivatized silica gel chromatographic support. 5μ Apex-ODS indicates an octadecylsilyl derivatized silica gel chromatographic support having a nominal particle size of 5μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev.) Celite® is a filter aid composed of acid-washed diatomaceous silica, and is a registered trademark of Manville Corp., Denver, Colo.

The following examples are illustrative of the present invention but not intended to be limiting in any way.

EXAMPLE 1

(R,S)-N-[4-(2-Nitro-4-trifluoromethylphenyl) morpholin-2-ylmethyl]-N-1,1-dimethyl-2-(4-methoxvphenyl)]ethylamine a) (R,S)-2-([1,1-dimethyl-2-(4-methoxyphenyl)] ethylcarbamoyl)-N-Boc-morpholine (R,S) Boc-2-carboxymorpholine (1.1 g, 4.7 mmol) was dissolved in CH$_2$Cl$_2$ (25 mL). Pyridine (0.6 mL, 7.1 mmol) was added, followed by drop-wise addition of cyanuric fluoride (0.63 g, 4.7 mmol). The reaction mixture was stirred for 2 h at RT. The reaction mixture was concentrated to dryness in vacuo then diluted with ethyl acetate and washed with water. The organic layers were dried (MgSO$_4$) and the solvent was evaporated to yield a colorless liquid that was dissolved in CH$_2$Cl$_2$ (10 mL) and added drop-wise to a solution containing 1,1-dimethyl-2-(4-methoxyphenyl) ethylamine (0.6 g, 4.7 mmol) and DIEA (0.7 mL, 4.7 mmol) in $CH_2Cl_2$ (25 mL). The reaction mixture was stirred for 18 h at RT. The reaction was washed with cold 1N HCl (2×50 mL), 1N NaOH (2×50 mL), brine (1×50 mL), dried over $MgSO_4$ and concentrated in vacuo to give a residue which was triturated with EtOAc to give the title compound as a white solid (1.34 mg, 73%). $H^1$-NMR (400 MHz, $CDCl_3$): δ 1.30 (s, 2H0, 1.34 (s, 3H), 1.47 (s, 9H), 2.69–2.87 (m, 2H), 2.93 (d, J=13.4 Hz, 1H), 3.02 (d, J=13.4 Hz, 1H), 3.50 (ddd, J=11.6, 11.6, 2.7 Hz, 1H), 3.75–3.79 (m, 1H), 3.79 (s, 3H), 3.85–3.95 (m, 2H), 4.37–4.33 (m, 1H), 6.81 (d, J=6.8 Hz, 2H), 7.14 (d, J=6.8 Hz, 2H).

b) (R,S)-2-([1,1-dimethyl-2-(4-methoxyphenyl)] ethylcarbamoyl)morpholine

The Boc protected amine from 1b (1.3 g, 3.3 mmol) was treated with 5 mL of 4M HCl solution in dioxane for 30 min. The solvent was eliminated and the residue was triturated with ether to obtain the title compound as a white solid (840 mg, 77%). MS (ES) m/e 293.1$[M+H]^+$ c) (R,S)-N-(2-Nitro-4-trifluoromethylphenyl)-2-([1,1-dimethyl-2-(4-methoxyphenyl)]ethylcarbamoyl)morpholine The free amine from Example 1b (200 mg, 0.6 mmol), 2-fluoro-1-nitro-5-trifluoromethylphenyl (136 mg, 0.66 mmol) and DIEA (157 mg, 1.2 mmol) were dissolved in acetonitrile. The reaction mixture was heated to reflux for 2 h. After cooling to RT, the solvent was eliminated the residue was dissolved in Ethyl Acetate, washed with water. The organic layer was dried ($MgSO_4$) and the solvent was evaporated to yield a yellow liquid that was purified by flash column chromatography (silica gel, 30% Ethyl acetate/hexanes) to obtain the title compound as a bright yellow liquid (327 mg, 100%). MS (ES) m/e 482.0 $[M+H]^+$ d) (R,S)-4-(2-Nitro-4-trifluoromethylphenylmorpholin-2-ylmethyl)-N-[1,1-dimethyl-2-(4-methoxyphenyl)] ethylamine To a cooled (0° C.) solution of compound from example 1c (277 mg, 0.57 mmol) in anhydrous THF under argon (5 mL) was added 0.69 mL of a 1M solution of diborane in THF. The reaction mixture was heated to reflux overnight. After cooling to room temperature methanol (5 mL) and cc HCl (0.3 mL) was added and the reaction mixture was heated to reflux for 30 min. The solvent was evaporated and the residue was dissolved in ethyl acetate, washed with $NaHCO_3$ solution, and brine. The combined organic layers were dried ($MgSO_4$) and the solvent was evaporated. The residue was purified by flash column chromatography (silica gel, 2% Methanol/$CH_2Cl_2$) to yield the title compound as a bright yellow liquid (40 mg, 46% yield based on recovered starting material). MS (ES) m/e 468.0 $[M+H]^+$

EXAMPLE 2

(R,S)-N-[4-(2,3-Dichlorobenzyl)morpholin-2-ylmethyl]-N-[1,1-dimethyl-2-(4-methoxyphenyl)] ethylamine a) (R,S)-N-(4-(2,3-Dichlorobenzyl)-2-([1,1-dimethyl-2-(4-methoxyphenyl)]ethylcarbamoyl)morpholine The amine from 1b (500 mg, 1.5 mmol) was dissolved in anhydrous methanol (25 mL) then 2,3-dichlorobenzaldehyde (266 mg, 1.5 mmol) and 4A molecular sieves were added after 10 min acetic acid (1.5 mmol) and sodium cyanoborohydride were added (94 mg, 1.5 mmol). The reaction mixture was stirred at RT overnight. The solvent was eliminated and the residue was diluted with ethyl acetate and washed with water. The combined organic layers were dried ($MgSO_4$) and the solvent was evaporated and the residue was purified by flash column chromatography (silica gel, 30% Ethyl Acetate/hexanes) to yield the title compound as a colorless liquid (300 mg, 82% yield based on recovered starting material). MS (ES) m/e 450.9 $[M+H]^+$ b) (R,S)-N-[4-(2,3-Dichlorobenzyl)morpholin-2-ylmethyl]-N-[1,1-dimethyl-2-(4-methoxyphenyl)]ethylamine.

Following analogous procedure as the one described in example 1d, compound 2a (210 mg, 0.47 mmol) was converted to the title compound (140 mg, 68%). MS (ES) m/e 437.1 $[M+]^+$ With appropriate manipulation and protection of any chemical functionality, synthesis of the remaining compounds of Formula (I) is accomplished by methods analogous to those above and to those described in the Experimental section.

In order to use a compound of Formula (I) or a pharmaceutically acceptable salt thereof for the treatment of humans and other mammals, it is normally formulated in accordance with standard pharmaceutical practice as a pharmaceutical composition.

The calcilytic compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various calcilytic compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered.

Preferably the composition is in unit dosage fortn. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula(I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease.

Diseases and disorders which might be treated or prevented, based upon the affected cells, include bone and mineral-related diseases or disorders; hypoparathyroidism; those of the central nervous system such as seizures stroke, head trauma, spinal cord injury, hypoxia-induced nerve cell damage, such as occurs in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney, such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea and spastic colon, GI ulcer diseases; GI diseases with excessive calcium absorption such as sarcoidosis; autoimmune diseases and organ transplant rejection; squamous cell carcinoma; and pancreatitis.

In a preferred embodiment of the present invention, the present compounds are used to increase serum parathyroid hormone ("PTH") levels. Increasing serum PTH levels can be helpful in treating diseases such as hypoparathyroidism, osteosarcoma, periodontal disease, fracture, osteoarthritis, rheumatoid arthritis, Paget's disease, humoral hypercalcemia malignancy and osteoporosis.

Another aspect of the present invention describes a method of treating a patient comprising administering to the patient an amount of a present compound sufficient to increase the serum PTH level. Preferably, the method is carried out by administering an amount of the compound effective to cause an increase in duration and/or quantity of serum PTH level sufficient to have a therapeutic effect.

In various embodiments, the compound administered to a patient causes an increase in serum PTH having a duration of up to one hour, about one to about twenty-four hours, about one to about twelve hours, about one to about six hours, about one to about five hours, about one to about four hours, about two to about five hours, about two to about four hours, or about three to about six hours.

In additional different embodiments, the compound administered to a patient causes an increase in serum PTH of up to two fold, two to five fold, five to ten fold, and at least 10 fold, greater than peak serum PTH in the patient. The peak serum level is measured with respect to a patient not undergoing treatment.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (I) are demonstrated by the following tests:

(I) Calcium Receptor Inhibitor Assay

Calcilytic activity was measured by determining the $IC_{50}$ of the test compound for blocking increases of intracellular $Ca^{2+}$ elicited by extracellular $Ca^{2+}$ in HEK 293 4.0–7 cells stably expressing the human calcium receptor. HEK 293 4.0–7 cells were constructed as described by Rogers et al., *J. Bone Miner. Res.* 10 Suppl. 1:S483, 1995 (hereby incorporated by reference herein). Intracellular $Ca^{2+}$ increases were elicited by increasing extracellular $Ca^{2+}$ from 1 to 1.75 mM. Intracellular $Ca^{2+}$ was measured using fluo-3, a fluorescent calcium indicator.

Cells were maintained in T-150 flasks in selection media (DMEM supplemented with 10% fetal bovine serum and 200 ug/mL hygromycin B), under 5% $CO_2$:95% air at 37° C. and were grown up to 90% confluency. The medium was decanted and the cell monolayer was washed twice with phosphate-buffered saline (PBS) kept at 37° C. After the second wash, 6 mL of 0.02% EDTA in PBS was added and incubated for 4 minutes at 37° C. Following the incubation, cells were dispersed by gentle agitation. Cells from 2 or 3 flasks were pooled and pelleted (100×g). The cellular pellet was resuspended in 10–15 mL of SPF-PCB+ and pelleted again by centrifugation. This washing was done twice.

Sulfate- and phosphate-free parathyroid cell buffer (SPF-PCB) contains 20 mM Na-Hepes, pH 7.4, 126 mM NaCl, 5 mM KCl, and 1 mM $MgCl_2$. SPF-PCB was made up and stored at 4° C. On the day of use, SPF-PCB was supplemented with 1 mg/mL of D-glucose and 1 mM $CaCl_2$ and then split into two fractions. To one fraction, bovine serum albumin (BSA; fraction V, ICN) was added at 5 mg/mL (SPF-PCB+). This buffer was used for washing, loading and maintaining the cells. The BSA-free fraction was used for diluting the cells in the cuvette for measurements of fluorescence.

The pellet was resuspended in 10 mL of SPF-PCB+ containing 2.2 uM fluo-3 (Molecular Probes) and incubated at room temperature for 35 minutes. Following the incubation period, the cells were pelleted by centrifugation. The resulting pellet was washed with SPF-PCB+. After this washing, cells were resuspended in SPF-PCB+ at a density of 1–2×106 cells/mL. For recording fluorescent signals, 300 uL of cell suspension were diluted in 1.2 mL of SPF buffer containing 1 mM $CaCl_2$ and 1 mg/mL of D-glucose. Measurements of fluorescence were performed at 37° C. with constant stirring using a spectrofluorimeter. Excitation and emission wavelengths were measured at 485 and 535 nm, respectively. To calibrate fluorescence signals, digitonin (5 mg/mL in ethanol) was added to obtain Fmax, and the apparent Fmin was determined by adding Tris-EGTA (2.5 M Tris-Base, 0.3 M EGTA). The concentration of intracellular calcium was calculated using the following equation:

Intracellular calcium=$(F-F_{min}/F_{max})\times K_d$; where $K_d$=400 nM.

To determine the potential calcilytic activity of test compounds, cells were incubated with test compound (or vehicle as a control) for 90 seconds before increasing the concentration of extracellular $Ca^{2+}$ from 1 to 2 mM. Calcilytic compounds were detected by their ability to block, in a concentration-dependent manner, increases in the concentration of intraceliular $Ca^{2+}$ elicited by extraceliular $Ca^{2+}$.

In general, those compounds having lower $IC_{50}$ values in the Calcium Receptor Inhibitor Assay are more preferred compounds. Compounds having an $IC_{50}$ greater than 50 uM were considered to be inactive. Preferred compounds are those having an $IC_{50}$ of 10 uM or lower, more preferred compounds have an $IC_{50}$ of 1 uM, and most preferred compounds have an $IC_{50}$ of 0.1 uM or lower.

(II) Calcium Receptor Binding Assay

HEK 293 4.0–7 cells stably transfected with the Human Parathyroid Calcium Receptor("HuPCaR") were scaled up in T180 tissue culture flasks. Plasma membrane is obtained by polytron homogenization or glass douncing in buffer (50 mM Tris-HCl pH 7.4, 1 mM EDTA, 3 mM $MgCl_2$) in the presence of a protease inhibitor cocktail containing 1 uM Leupeptin, 0.04 uM Pepstatin, and 1 mM PMSF. Aliquoted membrane was snap frozen and stored at −80° C. $^3H$ labeled compound was radiolabeled to a radiospecific activity of 44 Ci/mmole and was aliquoted and stored in liquid nitrogen for radiochemical stability.

A typical reaction mixture contains 2 nM $^3H$ compound ((R,R)-N-4'-Methoxy-t-3-3'-methyl-1'-ethylphenyl-1-(1-naphthyl)ethylamine), or $^3H$ compound (R)-N-[2-Hydroxy-3-(3-chloro-2-cyanophenoxy)propyl]-1,1-dimethyl-2-(4-methoxyphenyl)ethylamine 4–10 ug membrane in homogenization buffer containing 0.1% gelatin and 10% EtOH in a reaction volume of 0.5 mL. Incubation is performed in 12×75 polyethylene tubes in an ice water bath. To each tube 25 uL of test sample in 100% EtOH is added, followed by 400 uL of cold incubation buffer, and 25 uL of 40 nM $^3H$-compound in 100% EtOH for a final concentration of 2 nM. The binding reaction is initiated by the addition of 50 uL of 80–200 ug/mL HEK 293 4.0–7 membrane diluted in incubation buffer, and allowed to incubate at 4° C. for 30 min. Wash buffer is 50 mM Tris-HCl containing 0.1% PEI. Nonspecific binding is determined by the addition of 100-fold excess of unlabeled homologous ligand, and is generally 20% of total binding. The binding reaction is terminated by rapid filtration onto 1% PEI pretreated GF/C filters using a Brandel Harvestor. Filters are placed in scintillation fluid and radioactivity assessed by liquid scintillation counting.

Formulations for pharmaceutical use incorporating compounds of the present invention can be prepared in various forms and with numerous excipients. Examples of such formulations are given below.

Inhalant Formulation

A compound of Formula (I) (1 mg to 100 mg) is aerosolized from a metered dose inhaler to deliver the desired amount of drug per use.

Tablet Formulation

| Tablets/Ingredients | Per Tablet |
|---|---|
| 1. Active ingredient (Cmp. of Formula(I)) | 40 mg |
| 2. Corn Starch | 20 mg |
| 3. Alginic acid | 20 mg |
| 4. Sodium Alginate | 20 mg |
| 5. Mg stearate | 13 mg |

Procedure for Tablet Formulation

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

Parenteral Formulation

A pharmaceutical composition for parenteral administration is prepared by dissolving an appropriate amount of a compound of Formula (I) in polyethylene glycol with heating. This solution is then diluted with water for injections (to 100 ml). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound selected from Formula (I) hereinbelow:

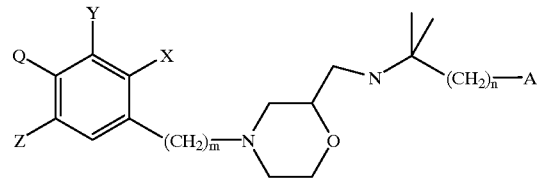

Formula (I)

or a pharmaceutically acceptable salt thereof, wherein:

m is an integer from 0 to 2;

n is an integer from 1 to 3;

X is selected from the group consisting of CN, $NO_2$, Cl, F, and H;

Y is selected from the group consisting of Cl, F, Br, I and H; and

Q and Z are, independently, selected from the group consisting of H, $R_1$, $SO_2R_1'$, $R_1C(O)OR_1''$, $SO_2NR_1'R_1''$, $C(O)NR_1'R_1''$, $NR_1'SO_2R_1''$, wherein R1, $R_1'$ and $R_1''$ are independently selected from the group consisting of hydrogen, $C_{1-4}$ alkyl, $C_{3-6}$ cycloalkyl, $C_{2-5}$ alkenyl, $C_{2-5}$ alkynyl, heterocycloalkyl, aryl and aryl $C_{1-4}$ alkyl; or $R_1'$ and $R_1''$ together form a 3 to 7 membered optionally substituted heterocyclic ring; wherein any substituents are selected from the group consisting of CN, aryl, $CO_2R$, $CO_2NHR$, OH, OR, $NH_2$, halo, $CF_3$, $OCF_3$ and $NO_2$; wherein R represents H, $C_{1-4}$ alkyl, and $C_{3-6}$ cycloalkyl; and A is phenyl or naphthyl, unsubstituted or substituted with any substituents being selected from the group consisting of OH, halo, $CO_2R_1$, $C_{1-4}$ alkyl, $C_{1-4}$ alkoxy, $C_{3-6}$ cycloalkyl, $OSO_2R_1$, CN, $NO_2$, $OCF_3$, $CF_3$, and $CH_2CF_3$, $(CH_2)_nCO_2H$, $(CH_2)_nCO_2R_1$, and $O-(CH_2)_n CO_2R_1$, wherein n is an integer from 0 to 3 0–3 and $R_1$ represents $C_{1-4}$ alkyl, $C_{3-6}$ cycloalkyl, $C_{3-6}$ cycloalkyl, heteroaryl or fused heteroaryl (wherein the hetero-ring contains N, O or S and is aromatic, dihydro or tetrahydro) unsubstituted or substituted with any substituents being selected from the group consisting of OH, $OCH_3$, $CH(CH_3)_2$, halo, $CO_2R_1$, $C_{1-4}$ alkyl, $C_{1-4}$ alkoxy, $C_{3-6}$ cycloalkyl, CN, $NO_2$, $OCF_3$, $CF_3$, $CH_2CF_3$, $(CH_2)_n CO_2R_1$, and $O-(CH_2)_n CO_2R_1$.

2. A compound according to claim 1 selected from the group consisting of: (R,S)-N-[4-(2-Nitro-4-trifluoromethylphenyl)morpholin-2-ylmethyl]-N-[1,1-dimethyl-2- (4-methoxyphenyl)]ethylamine; and (R,S)-N-[4-(2,3-Dichlorbenzyl)morpholin-2-ylmethyl]-N-[1,1-dimethyl-2- (4-methoxyphenyl)]ethylamine.

3. A method of antagonizing a calcium receptor which comprises administering to a subject in need thereof, an effective amount of a compound according to claim 1.

4. A method of treating an abnormal bone or mineral homeostasis disease or disorder, which comprises administering to a subject in need of treatment thereof an effective amount of a compound of claim 1.

5. A method according to claim 4 wherein the bone or mineral disease or disorder is selected from the group consisting of osteosarcoma, periodontal disease, fracture healing, osteoarthritis, rheumatoid arthritis, Paget's disease, humoral hypercalcemia, malignancy and osteoporosis.

6. A method according to claim 5 wherein the bone or mineral disease or disorder is osteoporosis.

7. A method of increasing serum parathyroid levels which comprises administering to a subject in need of treatment an effective amount of a compound of claim 1.

* * * * *